(12) United States Patent
Keller

(10) Patent No.: US 7,325,995 B2
(45) Date of Patent: Feb. 5, 2008

(54) APPLICATOR FOR A DISPENSING APPLIANCE

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 9 days.

(21) Appl. No.: 11/001,645

(22) Filed: Dec. 2, 2004

(65) Prior Publication Data
US 2005/0127119 A1    Jun. 16, 2005

(30) Foreign Application Priority Data
Dec. 12, 2003 (CH) .................................... 2122/03

(51) Int. Cl.
B05C 11/00 (2006.01)
B43K 1/06 (2006.01)
B65D 25/40 (2006.01)
(52) U.S. Cl. .................. 401/266; 401/265; 222/566
(58) Field of Classification Search ............ 401/5, 401/261–267; 222/566–574
See application file for complete search history.

(56) References Cited

U.S. PATENT DOCUMENTS

| 1,038,180 | A | * | 9/1912 | Moreland ................. 401/179 |
|---|---|---|---|---|
| 2,754,624 | A | * | 7/1956 | Wester ........................ 47/1.7 |
| 2,804,767 | A | | 9/1957 | Schoen |
| 2,882,716 | A | * | 4/1959 | Anderson, Sr. ............. 401/139 |
| 2,888,695 | A | * | 6/1959 | Anderson et al. ........... 401/266 |
| 4,887,924 | A | * | 12/1989 | Green ........................ 401/261 |
| 5,562,356 | A | * | 10/1996 | Hilbert ....................... 401/264 |
| 6,926,457 | B2 | * | 8/2005 | Vidal Esmoris ............... 401/1 |
| 2001/0003563 | A1 | * | 6/2001 | Schauer et al. ................ 401/5 |

FOREIGN PATENT DOCUMENTS

EP    1 157 748 A1    11/2001

* cited by examiner

Primary Examiner—David J. Walczak
(74) Attorney, Agent, or Firm—Foley & Lardner LLP

(57) ABSTRACT

The applicator for a double cartridge includes an adapter for connection to a mixer attached to a double cartridge as well as a dispensing slot, the side of the enclosure that is turned towards the glued substrate forming an angle with the longitudinal axis of the adapter which is comprised between 5° and 90°. The underside of the enclosure is essentially continuously curved. Due to the curvature of the enclosure, the material that is to be glued, e.g. lung tissue, is first smoothened and immediately thereafter evenly coated with adhesive. This allows a reliable application of such an applicator in medicine or in the industry.

13 Claims, 2 Drawing Sheets

FIG. 4A
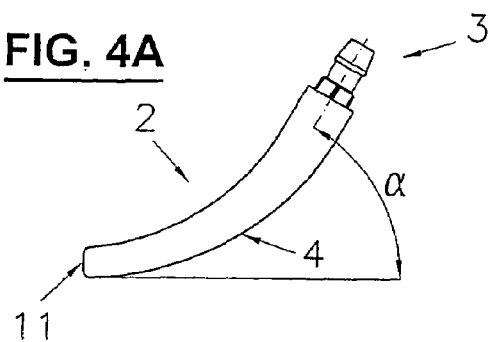
FIG. 6
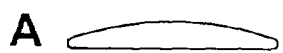
A
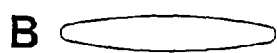
B
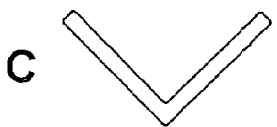
C
D
E
FIG. 4B
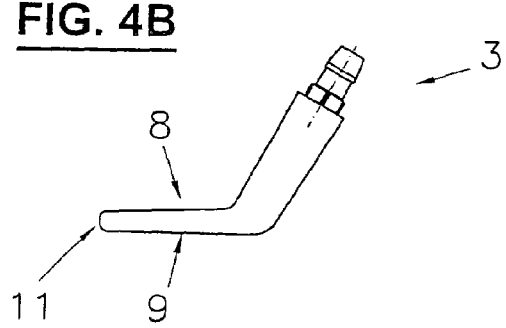
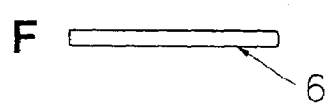
F
G
FIG. 4C
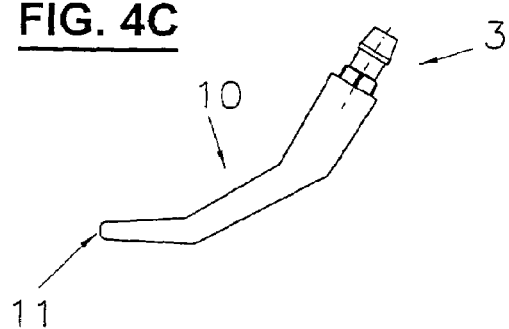
FIG. 5A       FIG. 5B       FIG. 5C
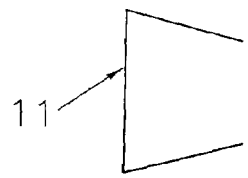   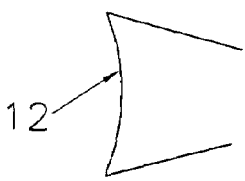   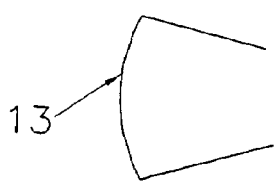

APPLICATOR FOR A DISPENSING APPLIANCE

FIELD OF THE INVENTION

The present invention refers to an applicator for a dispensing appliance, particularly for medicinal technique, including an adapter for connection to a mixer or to the dispensing appliance itself as well as a dispensing slot, the side of the enclosure of the applicator that is turned towards the glued substrate forming an angle with the longitudinal axis of the adapter.

The significance of gluing tissue such as lung, liver, or milt tissue is continuously increasing in medicine, but no devices designed for this particular purpose are known in the art so far and conventional attachments on mixers do not provide an adequate solution.

In a larger context, this is also true for applications such as cementing, coating or sealing fabrics, tarpaulins, foamed parts or similar materials having uneven surfaces.

PRIOR ART

An adapter for a static mixer is disclosed in the European Patent Application No. 1,210,985. The adapter disclosed in this reference is intended for the shaped discharge of a viscous mixture from the mixer, the outside of the latter being provided with line-shaped cutting guides for cutting it according to the desired opening width in a direction that is at least approximately parallel to that of the gap of the dispensing opening.

An applicator for the application of plaster, cement or mortar, is known from U.S. Pat. No. 2,804,767. The bottom side of this adapter forms an angle with the longitudinal axis of the appliance.

The European Patent Application No. 1,157,748 discloses an adhesive dispenser having an outlet portion whose bottom side includes a bend.

These appliances of the prior art are unsuitable for gluing or for a defined coating of uneven, sensitive and resilient surfaces such as lung tissue or the like since the main problem in this case is that such materials are very uneven and soft, thereby making an efficient and regular application of adhesives very problematic.

SUMMARY OF THE INVENTION

Based on this prior art, it is the object of the present invention to provide an applicator for a dispensing appliance that allows an efficient and gentle application of adhesives or sealants particularly to tissue such as lung or liver tissue or the like. This is accomplished by an applicator wherein the underside of the enclosure is curved and the curvature is essentially continuous.

BRIEF DESCRIPTION OF THE DRAWINGS

The invention will be explained in more detail hereinafter with reference to drawings of exemplary embodiments.

FIGS. 5A through 5C show three variants regarding the shape of the outlet,
and
FIGS. 6A through 6G show variants regarding the dispensing cross-section.

DETAILED DESCRIPTION OF PREFERRED EMBODIMENTS

Figure 1:
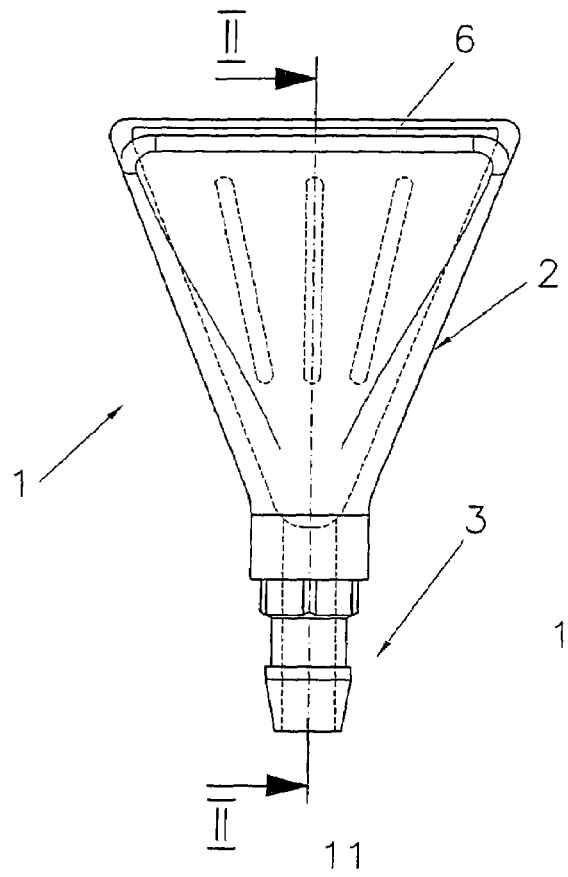
FIG. 1 shows an applicator of the invention in a top view.

Applicator 1 consists of a two-part enclosure 2 with adapter 3, enclosure 2 including a lower portion 4 and a cover-shaped upper portion 5. As appears in FIG. 1, enclosure 2 is conically enlarged outwardly, i.e. towards dispensing slot 6.

Figure 2:
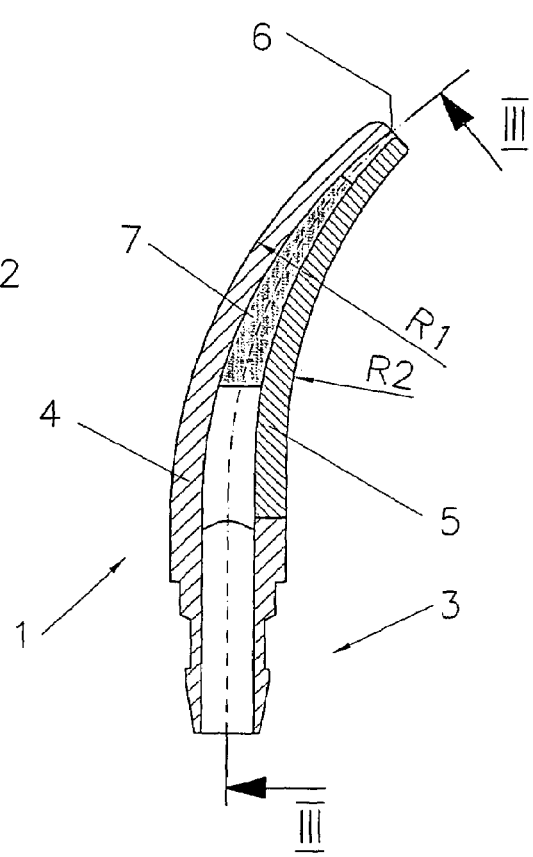
FIG. 2 shows a section according to line II-II in FIG. 1.
Figure 3:
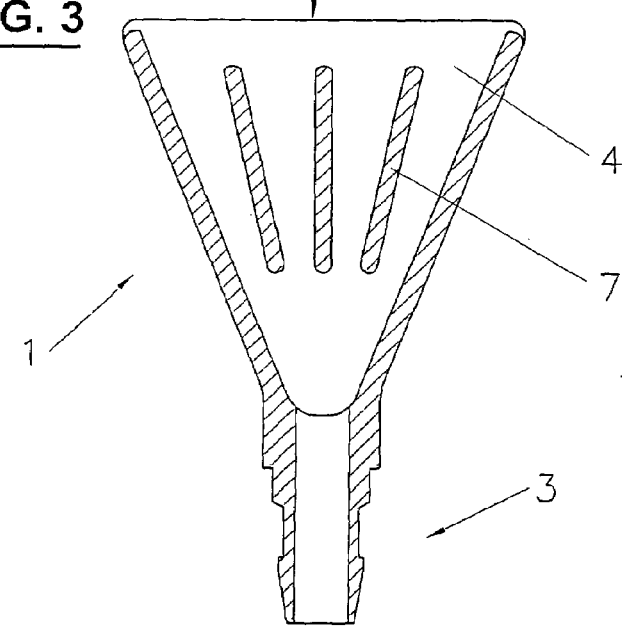
FIG. 3 shows a section according to line III-III in FIG. 2,
FIGS. 4A through 4C show three variants regarding the shape of the enclosure of the applicator.

In the exemplary embodiment shown in FIGS. 1 to 3, the width of the slot may be 12 or 16 mm and its thickness may be comprised between 0.1 and 0.3 mm. The lower and upper sides of the enclosure are defined according to the parts that are to be glued, enclosure portion 4 being intended to come into contact with the tissue, e.g. lung tissue, and thus being the lower portion, while portion 5 correspondingly represents the upper portion.

Figure 2A:
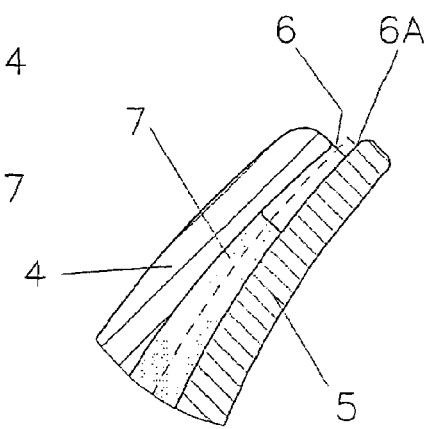
FIG. 2A shows an enlarged detail of a variant of the outlet end.

As appears in FIG. 2A, upper portion 5 may possibly be a little longer than lower portion 4, the difference 6A being 0.5 mm in the present example. In certain cases, it is thus achieved that the adhesive dispensed from dispensing slot 6 is directed towards the tissue.

As further appears in FIG. 2, at least the lower enclosure side 4 is curved, the curvature having the shape of a circle arc with a defined radius, another elliptical or parabolic shape, or a discontinuous one, formed of one or several bends. It is important here that the longitudinal axis of adapter 3 forms an angle with the surface that is to be glued resp. with the lower portion 4 of the enclosure, which angle may vary according to the intended application. The smoothening function also depends on the surface structure and the constituent material of the lower portion of the enclosure.

In FIG. 3, the lower enclosure portion 4 is shown from the inside and three guiding walls 7 are illustrated. The function of these guiding walls is to distribute the adhesive coming from the adapter in order to achieve a regular discharge.

Adapter 3 is designed for being inserted into the outlet of a mixer, but it is understood that adapters of other dimensions and designs are possible to allow the connection to a particular mixer or dispenser.

As mentioned above, enclosure 2 is composed of two parts that are manufactured separately, upper portion 5, which is designed as a cover, being fitted on lower portion 4 shown in FIG. 3 and connected thereto. The connection may be established in various ways, e.g. by cementing or ultrasonic welding, inter alia.

During the application of an adhesive to a tissue having an uneven surface, the tissue is smoothened by the curvature of lower portion 4 before the adhesive is dispensed. Due to the conically enlarged shape of the enclosure and a continuously diminishing total cross-sectional area, on one hand, and due to the presence of guiding walls, on the other hand, a steady, regular flow of the adhesive onto the smoothened underlying material is obtained while the height of the dispensing slot is a function both of the viscosity and of the required dispensing volume. In some applications, the length of salient portion 6A may have a certain influence.

Based on the described exemplary embodiment according to FIGS. 1 to 3, many variations are possible for applications in medicinal technique or in the industry. As shown in FIG. 4A, enclosure 2 may have a continuous curvature, while enclosure 8 according to FIG. 4B, i.e. at least its underside 9, and enclosure 10 according to FIG. 4C have one or two bends, respectively, and all variations between a continuous and a discontinuous curvature and a plurality of bends are possible. In all cases, the angle α between the longitudinal axis of adapter 3 and the dispensing end 11 of the lower portion may be comprised between 5° and 90°, preferably between 10° and 90°.

As shown in FIGS. 5A through 5C, dispensing end 11 may be straight as in FIG 5A, concave as dispensing end 12 in FIG. 5B, or convex as dispensing end 13 in FIG. 5C.

FIGS. 6A through 6G show different possible cross-sections of the dispensing slot, FIG. 6F corresponding to the cross-section of dispensing slot 6.

Depending on the intended application, a large range of variations of the cross-section of the dispensing slot, of the dimensions of the guiding walls etc. from the lower millimeter range up to the range of some hundreds of millimeters are possible.

What is claimed is:

1. An applicator for dispensing material from a dispensing appliance or a mixer onto a substrate for a medicinal technique, comprising:
   an enclosure having a lower portion configured to face toward the substrate and an opposing upper portion;
   an adapter having a longitudinal axis and configured to connect to the mixer or dispensing appliance;
   a dispensing slot defined by respective terminal end portions of the upper portion and the lower portion of the enclosure where the upper and lower portions converge at a tip at a dispensing end of the enclosure, wherein the dispensing slot is located off the longitudinal axis of the adapter;
   wherein the lower portion of the enclosure has an essentially continuous curvature at a first radius adapted to smooth the substrate to which the material is to be applied, and forms an angle with the longitudinal axis of the adapter, and
   wherein the upper portion has an essentially continuous curvature at a second radius.

2. The applicator of claim 1, wherein the angle is between 5° and 90°.

3. The applicator of claim 1, wherein said enclosure is conically enlarged towards the dispensing slot.

4. The applicator of claim 1, wherein the lower portion has an inner surface including a plurality of guiding walls, wherein the plurality of guiding walls forms a plurality of channels in the enclosure which lead to the dispensing slot.

5. The applicator of claim 1, wherein the terminal end portion of the upper portion is longer than the terminal end portion of the lower portion.

6. The applicator of claim 5, wherein the end portion of the upper portion is about 0.5 mm longer than the end portion of the lower portion.

7. The applicator of claim 1, wherein the dispensing end has one of a straight, concave, or convex shape.

8. The applicator of claim 1, wherein the dispensing slot has a cross-section that has one of a rectangular, angled, entirely-arc, or oval shape.

9. The applicator of claim 1, wherein the applicator is configured to dispense onto a tissue.

10. The applicator of claim 9, wherein the tissue has an uneven surface.

11. The applicator of claim 1, wherein the applicator is configured to dispense an adhesive.

12. The applicator of claim 1, wherein the applicator is configured to dispense a sealant.

13. The applicator of claim 1, wherein the slot has a width between 12 and 16 mm and a thickness of between 0.1 and 0.3 mm.

* * * * *